US012618763B2

(12) United States Patent
Shen et al.

(10) Patent No.: US 12,618,763 B2
(45) Date of Patent: May 5, 2026

(54) EXPERIMENTAL DEVICE AND METHOD FOR CHARACTERIZATION OF PARTICLE PACKING GRADATION

(71) Applicant: ANHUI NORMAL UNIVERSITY, Wuhu (CN)

(72) Inventors: Yeqing Shen, Wuhu (CN); Chao Zhai, Wuhu (CN); Mei Meng, Wuhu (CN)

(73) Assignee: ANHUI NORMAL UNIVERSITY, Wuhu (CN)

( * ) Notice: Subject to any disclaimer, the term of this patent is extended or adjusted under 35 U.S.C. 154(b) by 373 days.

(21) Appl. No.: 18/366,479

(22) Filed: Aug. 7, 2023

(65) Prior Publication Data

US 2024/0053242 A1     Feb. 15, 2024

(30) Foreign Application Priority Data

Aug. 15, 2022     (CN) .......................... 202210976423.1

(51) Int. Cl.
| | |
|---|---|
| *G01N 15/08* | (2006.01) |
| *G01N 15/02* | (2024.01) |
| *G01N 15/04* | (2006.01) |
| G01N 33/38 | (2006.01) |

(52) U.S. Cl.
CPC ............. *G01N 15/02* (2013.01); *G01N 15/04* (2013.01); *G01N 15/082* (2013.01); *G01N 15/0826* (2013.01); *G01N 15/088* (2013.01); *G01N 33/383* (2013.01)

(58) Field of Classification Search
CPC ............. G01N 15/082; G01N 15/0826; G01N 15/088; G01N 15/04; G01N 33/383
See application file for complete search history.

(56) References Cited

U.S. PATENT DOCUMENTS

| | | | | |
|---|---|---|---|---|
| 2,345,935 A | * | 4/1944 | Hassler .............. | G01N 15/0826 73/38 |
| 5,513,515 A | * | 5/1996 | Mayer ................ | G01N 15/0826 73/38 |
| 5,591,898 A | * | 1/1997 | Mayer ................ | G01N 15/0826 73/38 |

FOREIGN PATENT DOCUMENTS

| | | | | |
|---|---|---|---|---|
| CN | 203069487 U | * | 7/2013 | |
| KR | 101523067 B1 | * | 5/2015 | ............. G01N 33/42 |

OTHER PUBLICATIONS

ASTM International Standard C204-17. Standard Test Methods for Fineness of Hydraulic Cement by Air-Permeability Apparatus. ASTM International, Dec. 1, 2017.*

* cited by examiner

*Primary Examiner* — Herbert K Roberts
(74) *Attorney, Agent, or Firm* — Merchant & Gould P.C.

(57) ABSTRACT

The present invention discloses an experimental device for characterization of particle packing gradation. The device is provided with a filling container with an upper opening, an air-permeable thin plate is arranged in the filling container, the air-permeable thin plate is densely covered with air-permeable round holes, the bottom of the filling container communicates with the top of a connecting pipe, the bottom of the connecting pipe is connected to one end of a U-shaped pipe, a marking line is provided on the pipe wall of the U-shaped pipe on the side of the connecting pipe, the connecting pipe is provided with a three-way pipe with a valve, and the three-way pipe with a valve is connected to a vacuum pump in a main machine through a bypass. The present invention further provides an experimental method for characterizing particle packing gradation.

9 Claims, 1 Drawing Sheet

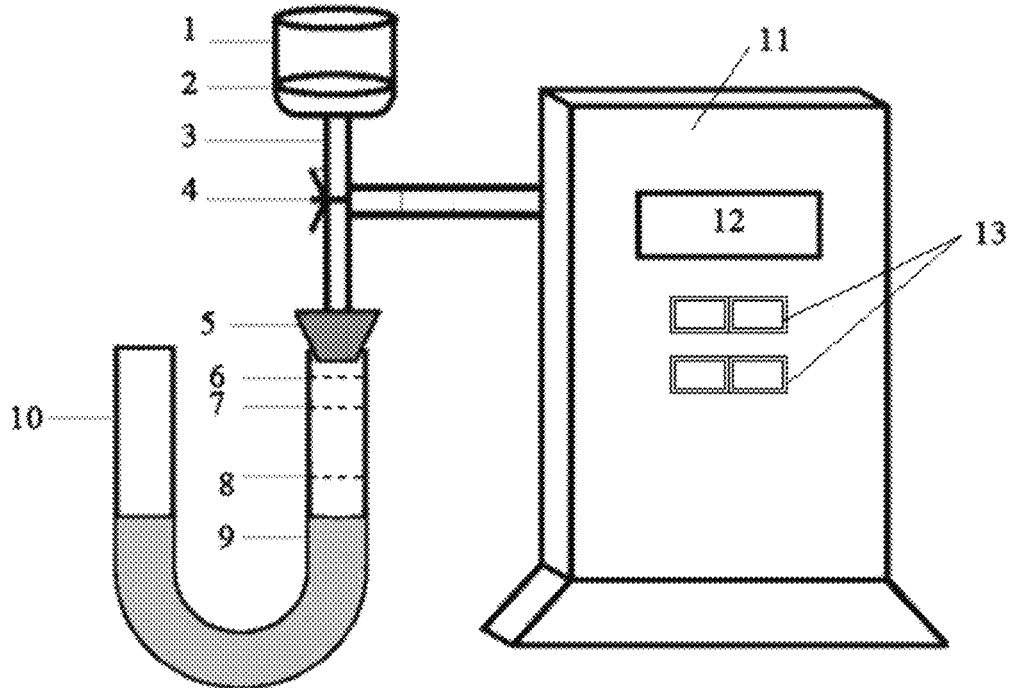

EXPERIMENTAL DEVICE AND METHOD FOR CHARACTERIZATION OF PARTICLE PACKING GRADATION

CROSS REFERENCE TO RELATED APPLICATIONS

This application claims the priority of Chinese Patent Application No. 202210976423.1, filed with the China National Intellectual Property Administration on Aug. 15, 2022, and titled with "EXPERIMENTAL DEVICE AND METHOD FOR CHARACTERIZATION OF PARTICLE PACKING GRADATION", which is hereby incorporated by reference in its entirety.

FIELD

The present invention relates to the technical field of experimental device, and in particular to an experimental device for characterization of particle packing gradation.

BACKGROUND

Particles are often used as raw materials in chemical, building materials and metallurgical industries. The final performance of the products converted from particles is closely related to particle packing. Particle packing gradation is an important factor for material engineering to obtain durability, compactness and other excellent performance. The regulation of particle packing and optimization of product performance both require the particle packing gradation. The current conventional equipment cannot directly test the particle packing gradation.

In industrial practice and application, the particle size distribution of particles is usually determined using laser particle size analysis. Then the particle size composition is adjusted according to the Fuller curve, to achieve continuous distribution of particles as much as possible, so as to obtain theoretically graded particles. However, the graded particles are not necessarily densely packed according to the order of the gradation degree. The particle size of the particles obtained by the laser particle size method is a theoretical particle size, which much differs from the real shape and size of the particles. The graded particles formulated according to the Fuller curve are only a rough approximation of the theory. In addition, the formulation method of the particle gradation according to the Fuller curve cannot be applied to particles with a wide particle size range.

The finer the capillary pores of the compacted particle packing structure and the more the number of the capillary pores, the longer the duration for a certain amount of air passing through. The duration for a certain amount of air passing through the packing pores of the compacted particles is closely related to the particle packing gradation. When the particles are packed up in the order of particle size, the formed packing pores are small and narrow, and the resistance to gas passage is large and the time taken is long. When the particles are packed up thicker and thicker in the order of particle size, the formed packing pores are smaller and narrower, and the resistance to gas passage is greater and the time taken is longer.

SUMMARY

The technical problem to be solved by the present invention is to provide a characterization method based on the actual particle packing gradation by utilizing the law of air passing through the particle packing structure, and its realization device.

In order to achieve the above object, the technical solution adopted in the present invention provides an experimental device for characterization of particle packing gradation, wherein the device is provided with a filling container with an upper opening, an air-permeable thin plate is arranged in the filling container, the air-permeable thin plate is densely covered with air-permeable round holes, the bottom of the filling container communicates with the top of a connecting pipe, the bottom of the connecting pipe is connected to one end of a U-shaped pipe, a marking line is provided on the pipe wall of the U-shaped pipe on the side of the connecting pipe, the connecting pipe is provided with a three-way pipe with a valve, and the three-way pipe with a valve is connected to a vacuum pump in a main machine through a bypass.

The filling container has a cylindrical or cuboid structure, the inner wall of the filling container is provided with a protruding platform for supporting an air-permeable thin plate, the air-permeable thin plate is placed on the platform, the distance between the air-permeable thin plate and the top of the connecting pipe is 1-2 cm, the thickness of the filling container wall and the thickness of the air-permeable thin plate are 0.5-1.5 cm, the thickness of the platform is 0.1-1.0 times the thickness of the filling container wall, the filling container above the air-permeable thin plate is provided with a depth scale on the inner wall, the minimum scale of the depth scale is 1 mm, the filling container is used for holding particles, the particle size of the particles is within the range of 0.01 mm-2 cm, the inner diameter of the filling container is 2-20 times the maximum particle size of the particles held in the filling container, the minimum inner diameter of the filling container is 2 cm, the height of the filling container above the air-permeable thin plate and the thickness of the filler layer are in a ratio of 1.0-1.5, the filling container and the connecting pipe are integrally cast and formed, and the area between the bottom of the platform of the filling container and the connecting pipe has a bucket-shaped structure with a large top and a small bottom.

The number of the air-permeable round holes on the air-permeable thin plate is 20-70 holes/cm², the diameter of the air-permeable round holes is 0.1-0.5 mm, 1-3 layers of qualitative filter paper are placed on the air-permeable thin plate, and the device is provided with a bracket supporting the filling container.

The connecting part of the connecting pipe and the U-shaped pipe is provided with a rubber plug, the center of the rubber plug is provided with a through hole, the bottom of the connecting pipe is inserted into the through hole, the outer edge of the rubber plug is inserted into the U-shaped pipe, and the rubber plug provides the connecting part of the connecting pipe and the U-shaped pipe with airtightness.

The diameter of the U-shaped pipe is 3-50 times the maximum particle size of the particles, the height of the U-shaped pipe is 20-600 times the maximum particle size of the particles, three marking lines are provided, which are, from top to bottom, the first marking line, the second marking line, and the third marking line, wherein the first marking line is at a position 0.8-0.9 times the total height of the U-shaped pipe, the second marking line is at a position 0.7-0.8 times the total height of the U-shaped pipe, and the third marking line is at a position 0.5-0.7 times the total height of the U-shaped pipe.

The U-shaped pipe is filled with a liquid to a height 0.3-0.5 times the total height of the U-shaped pipe, and the liquid is deionized water or pure water.

A vacuum pump and a power supply are fixed inside the casing of the main machine, a screen for displaying time is provided on the surface of the casing, the power supply supplies power for the vacuum pump and the screen, a button area is provided on the surface of the casing, and buttons for controlling timing and running of the vacuum pump are arranged in the button area.

An experimental method for characterizing particle packing gradation using an experimental device for characterization of particle packing gradation, comprising the following steps:

Step 1, filling a layer of fillers in a filling container;

Step 2. controlling a three-way pipe with a valve to connect a vacuum pump to a U-shaped pipe, and turning on the vacuum pump until a liquid level crossing the second marking line;

Step 3. controlling the three-way pipe with a valve to connect the filling container to the U-shaped pipe, and starting timing when the liquid level dropping to the second marking line;

Step 4. stopping timing when the liquid level dropping to the third marking line;

Step 5. repeating steps 2-4 until reaching the preset number of repeated measurements, and taking the arithmetic mean as the final test result;

Step 6. repeating steps 1-5 until the number of filler layers reaching the designed number of layers.

In the step 1, the thickness of each filler layer is 1.1-2.0 times the maximum particle size of the particles, the minimum thickness is 0.5 cm, each filler layer is compacted under a pressure of 1-20 MPa, and the total thickness of the fillers stacked layer-by-layer is 8-20 times the thickness of a single layer;

in the step 5, the number of repeated measurements is 3-5, and if the error of each repeated measurement is 1-2 s, it is qualified, otherwise it is unqualified.

Before the experiment, it is necessary to test the airtightness of the device. During the test, a liquid is injected into the U-shaped pipe, the U-shaped pipe is connected to the connecting pipe with a rubber plug, the vacuum pump is connected to the U-shaped pipe by controlling the three-way pipe with a valve, the vacuum pump is turned on, and the vacuum pump is turned off when the water level on one side of the U-shaped pipe crosses the first marking line. If there is no change in the liquid level for the set time, the airtightness of the device is qualified, and the characterization experiment of particle packing gradation can be carried out. The corresponding values of the packing thickness and air permeability time are obtained through the experimental method for characterizing particle packing gradation, so as to obtain the matching relationship between the specific value and the packing gradation index.

The present invention detects the duration for a certain amount of air passing through the packing pores of the compacted particle layer by layer, and calculates the ratio of the increased duration of air passing through the particle packing structure to the increased thickness layer by layer, and the arithmetic mean value of the ratio of each layer is taken to obtain a gradation index of the particle packing, which reflects the gradation state of the actual packing of the particles.

BRIEF DESCRIPTION OF DRAWINGS

The following is a brief description of the content expressed in each drawing in the specification of the present invention and the reference signs in the FIGURE:

FIG. 1 is a schematic diagram of the structure of an experimental device for characterization of particle packing gradation;

the reference signs in the above FIGURE are as follows: 1. filling container; 2. air-permeable thin plate; 3. connecting pipe; 4. three-way pipe with a valve; 5. rubber plug; 6. the first marking line; 7. the second marking line; 8. the third marking line; 9. liquid; 10. U-shaped pipe; 11. main machine; 12. screen; 13. button area.

DETAILED DESCRIPTION

Referring to the drawings, the specific embodiments of the present invention including the shape, structure, mutual position and connection relationship of each part, the function and working principle of each part, the manufacturing process, and the method of operation and use are further described in detail through the description of the embodiments, so as to help those skilled in the art have a more complete, accurate and in-depth understanding of the inventive concepts and technical solutions of the present invention.

As shown in FIG. 1, the experimental device for characterization of particle packing gradation is provided with a filling container 1 with an upper opening. The upper part of the filling container 1 is a metal cylinder or cuboid. The inner wall of the filling container near the bottom is provided with a protruding platform for supporting an air-permeable thin plate 2. The platform can be formed by a plurality of protruding points, or a circle of convex ring structure. The air-permeable thin plate 2 is also made of metal material, which has an overall shape of the edge fitting with the filling container 1. The air-permeable thin plate 2 is horizontally placed on the platform and can be removed from the platform, which has a detachable structure, and makes it convenient to clean. The air-permeable thin plate 2 is densely covered with air-permeable round holes, and generally it is necessary to place 1-3 layers of qualitative filter paper on the air-permeable thin plate 2 during use. The bottom of the filling container 1 is connected to the top of the connecting pipe 3, that is, the filling container 1, as a whole, is in a structure with both upper and lower openings. The particles are placed in the middle of the filling container 1 through the air-permeable thin plate 2. The bottom of the connecting pipe 3 is connected to one end of the U-shaped pipe 10, and a marking line is provided on the pipe wall of the U-shaped pipe 10 on the side of the connecting pipe 3. The connecting pipe 3 is provided with a three-way pipe 4 with a valve, that is, the middle of the connecting pipe 3 is cut off, and the cut-off part is connected to two interfaces of the three-way pipe 4 with a valve, and the other interface of the three-way pipe 4 with a valve is connected to a vacuum pump inside the main machine 11 through a hose.

A vacuum pump and a power supply are fixed in the casing of the main machine 11, and the surface of the casing is provided with the screen 12 for displaying timing. The power supply supplies power for the vacuum pump and the screen 12. A button area 13 is provided on the surface of the casing. Buttons for controlling timing and running of the vacuum pump are arranged in the button area 13. In this way, the timing can be controlled through the buttons, and the vacuum pump can also be controlled at the same time, which is convenient for experimental operation. The three-way pipe 4 with a valve can control two passage states, one is to make the vacuum pump communicate with the U-shaped pipe 10, and the other is to make the filling container 1 communicate with the U-shaped pipe 10.

The experimental device for characterization of particle packing gradation has requirements on parameters. Therefore, for different experimental particles, it is necessary to select different sizes of experimental devices for characterization of particle packing gradation. In particular, the inner diameter of the filling container 1 is 2-20 times the maximum particle size of the particles. If the minimum inner diameter of the filling container 1 is less than 2 cm, 2 cm is set as the minimum diameter of the container. The height of the filling container 1 above the air-permeable thin plate 2 is 1.0-1.5 times the thickness of the filler layer. The distance between the bottom of the air-permeable thin plate 2 and the top of the connecting pipe 3 is 1-2 cm. The thickness of the wall of the filling container 1 and the thickness of the wall of the air-permeable thin plate 2 are 0.5-1.5 cm. The size of the platform is 0.1-1.0 times the thickness of the wall. The diameter of the connecting part between the bottom of the filling container 1 and the connecting pipe 3 is 0.5-1.0 cm. A depth scale with a minimum scale of 1 mm is engraved on the filling container 1 above the air-permeable thin plate 2. The air-permeable thin plate 2 is evenly covered with air-permeable round holes with a diameter of 0.1-0.5 mm, and the number of the round holes is 20-70 holes/cm$^2$.

The diameter of the U-shaped pipe 10 is 3-50 times the diameter of the maximum particle size of the particles. The height of the U-shaped pipe 10 is 20-600 times the diameter of the maximum particle size of the particles. The first marking line 6 is at a position 0.8-0.9 times the total height of the U-shaped pipe 10, the second marking line 7 is at a position 0.7-0.8 times the total height of the U-shaped pipe 10, and the third marking line 8 is at a position 0.5-0.7 times the total height of the U-shaped pipe 10. The U-shaped pipe 10 is filled with a liquid 9 to a height 0.3-0.5 times the total height of the U-shaped pipe 10, and the liquid is generally deionized water or pure water. The power of the vacuum pump is determined according to the size of the U-shaped pipe 10, and is generally selected within the range of 5-500 W.

In order to ensure airtightness, the connecting part of the connecting pipe 3 and the U-shaped pipe 10 is provided with a rubber plug 5, the center of the rubber plug 5 is provided with a through hole. The bottom end of the connecting pipe 3 is inserted into the through hole, and the outer wall of the connecting pipe 3 has an interference fit with the through hole. The outer edge of the rubber plug 5 is inserted into the U-shaped pipe 10. The rubber plug 5 provides the connecting part of the connecting pipe 3 and the U-shaped pipe 10 with airtightness. Before each use of the device, a test on airtightness is required. First, the three-way pipe 4 with a valve is controlled to connect the vacuum pump to the U-shaped pipe 10, and then the vacuum pump is turned on. The vacuum pump is turned off when the water level on one side of the U-shaped pipe crosses the first marking line 6. The U-shaped pipe is quickly connected to the upper-sealed filling container using the three-way pipe. If there is no change in the liquid level for 60-120 s, the airtightness of the device is considered to be qualified.

When using the experimental device for characterization of particle packing gradation to carry out the experimental method for characterization of particle packing gradation, the thickness of the filler layer required to be filled layer-by-layer is 1.1-2.0 times the maximum particle size of the particles. If the thickness of a single layer is less than 0.5 cm, 0.5 cm is set as the minimum thickness. The total thickness of the fillers stacked layer-by-layer is 8-20 times the thickness of a single layer. The particles of each filling are compacted under a pressure of 1-20 MPa. Since each layer of particles needs to be compacted each time, the device is provided with a bracket for supporting the filling container 1 to provide support for the compaction.

First, the three-way pipe 4 with a valve is controlled to communicate the vacuum pump with the U-shaped pipe 10, and then the vacuum pump is turned on. The vacuum pump is turned off when the liquid level crosses the second marking line 7. Then the three-way pipe 4 with a valve is controlled to make the filling container 1 communicate with the U-shaped pipe 10. The liquid level continues to rise for a certain distance under the action of inertia and then begins to fall. When the liquid level drops to the second marking line, the stopwatch is started for timing. When the liquid level drops to the third marking line 8, the timing is stopped.

The test is repeated 3-5 times, and error of each test of 1-2 s is qualified. The arithmetic mean is taken as the final test result. If the test error is large, it is necessary to measure the airtightness of the device and analyze the rationality of matching of each technical parameter of the device. The thickness of the first layer of filled particles is measured using a vernier caliper. The measurement is repeated 3-5 times, and error of each measurement of 0.01-0.10 mm is qualified. The arithmetic mean value is taken as the final test result. The test results of the thickness of the filling particles and the air permeability time are listed in Table 1. The second layer of particles to be tested is filled and compacted. The above operation is repeated. The data of the test results are listed in Table 1. Finally, the particles filled in the metal container are cleaned up.

The thickness listed in Table 1 is the X-axis, the air permeability time is the Y-axis, (x1, y1) is the coordinate point measured on the first layer of particles, and (x2, y2) is the coordinate point measured on the second layer of particles, and so on. The slopes of the line segments passing through (x1, y1) point and (x2, y2) point, (x2, y2) point and (x3, y3) point, and so on, is calculated point-by-point. The arithmetic mean value of the slope of the line segment of each layer is calculated, which is an indicator that characterizes the actual particle packing gradation. The particle size of the particles ranges from 0.01 μm to 2 cm, preferably from 11 μm to 1 cm.

TABLE 1

| | Data of air permeability test | | | |
|---|---|---|---|---|
| | The first layer of particles | The first and second layers of particles | The first, second and third layers of particles | . . . |
| Thickness/mm | | | | |
| Air perme-ability time/s | | | | |
| Slope | — | | | |
| Average slope/indicator of packing gradation | | | | |

The experimental data can be recorded conveniently by filling in Table 1, and the required data results can be calculated.

It is illustrated below with reference to different examples.

Example 1

Chemically pure reagents nickel particles and iron particles were used, where the particle size of the nickel particles was within the range of 1-30 nm, and the particle size of the iron particles was within the range of 150-500 μm. The nickel particles and iron particles were evenly mixed according to the weight ratio of 3:7. The inner diameter of the filling part of the filling device was 2 cm, the diameter of the neck was 0.5 cm, the diameter of the air-permeable hole of the air-permeable thin plate 2 was 0.6 mm, the number of air-permeable round holes was 30/cm², and the air-permeable thin plate 2 was covered with 2 layers of qualitative filter paper.

The bottom of the filling container 1, the connecting pipe 3, the three-way pipe 4 with a valve, the U-shaped pipe 10 the same way. The data of the test results are listed in Table 2. Finally, the particles filled in the metal container was cleaned up.

The slopes of the ten line segments passing through (0.51, 21) point and (1.00, 62) point, (1.00, 62) point and (1.52, 91) point, and so on, were calculated point-by-point. The arithmetic mean value of the slopes of the ten line segments was calculated, and the result is also listed in Table 2. An indicator that characterizes the actual particle packing gradation was obtained.

TABLE 2

| Data of test in Example 1 | | | | | | | | | | |
|---|---|---|---|---|---|---|---|---|---|---|
| | One layer | Two layers | Three layers | Four layers | Five layers | Six layers | Seven layers | Eight layers | Nine layers | Ten layers |
| Thickness/cm | 0.51 | 1.00 | 1.52 | 2.02 | 2.51 | 3.00 | 3.52 | 4.05 | 4.52 | 5.01 |
| Air permeability time/s | 21 | 62 | 91 | 118 | 144 | 160 | 173 | 184 | 189 | 194 |
| Slope point by point | — | 84 | 56 | 54 | 53 | 33 | 25 | 21 | 11 | 10 |
| Average slope/indicator of gradation | | | | | | 38 | | | | | and the main machine 11 were connected to each other. The U-shaped pipe 10 was placed vertically and parallel to the main machine 11. The diameter of the U-shaped pipe 10 was 1 cm, and the height of the U-shaped pipe 10 was 15 cm. Three marking lines were designed on the U-shaped pipe 10 on the side close to the main machine 11. From top to bottom, the first marking line 6 was at a height of 13 cm, the second marking line 7 was at a height of 11 cm, and the third marking line 8 was at a height of 9 cm. The U-shaped pipe 10 was filled with deionized water to a height of 6 cm. The main machine 11 was connected with a vacuum pump and an electrical control device, where the power of the vacuum pump was 50 W.

The upper opening of the filling container was sealed with a large sealing rubber plug. The vacuum pump of the main machine 11 was turned on. The vacuum pump was turned off when the water level on one side of the U-shaped pipe 10 crossed the first marking line 6. The U-shaped pipe was quickly connected to the upper-sealed filling container using the three-way pipe. There was no change in the liquid level for 100 s, and the airtightness of the device was qualified.

The large sealing rubber plug was removed. 4.7 g of the first layer of nickel-iron mixed particles was filled. The particle packing layer was compacted under a pressure of 3 MPa.

The vacuum pump was turned on. When the liquid level crossed the second marking line 7, the vacuum pump was turned off. The U-shaped pipe and the filling container were quickly connected using the three-way pipe. The liquid level continued to rise for a certain distance under the action of inertia and then began to fall. When the liquid level dropped to the second marking line, the stopwatch was started for timing. When the liquid level dropped to the third marking line 8 at 21 s, the timing was stopped. The experiment was repeated 3 times, the timing was stopped at 20 s, 21 s and 21 s respectively. The average value of 21 s was used as the final test result. The thickness of the first layer of filled particles was randomly measured three times using a vernier caliper, which were 0.52, 0.50, and 0.51 cm respectively, and 0.51 cm was taken as the final test result. The second layer of iron-nickel mixed particles was filled and compacted in Example 2

Industrially pure chemical reagents $ZrO_2$ particles, SiC particles, $TiO_2$ particles, redispersible latex particles and mullite particles were used, and the particle size of each particle was within the range of 60-120 mesh. The chemical composition of the redispersible latex particles was mainly acrylic acid copolymer. The above particles were evenly mixed in a weight ratio of 1:1:1:0.1:2. The filling part of the filling device had a diameter of 2 cm and a total height of 5 cm. The distance between the air-permeable thin plate 2 and the neck was 1 cm. The filling container 1 and the air-permeable thin plate 2 had a thickness of 1.5 cm. The size of the platform was 10 mm. A depth scale with a minimum scale of 1 mm was engraved on the inner side of the particle filling part of the metal container. The diameter of the neck of the lower part of the metal container was 0.6 cm. The diameter of the air-permeable holes of the air-permeable thin plate 2 was 0.2 mm. The number of the air-permeable round holes was 40/cm². The air-permeable thin plate 2 was covered with 3 layers of qualitative filter paper.

The bottom of the filling container 1, the connecting pipe 3, the three-way pipe 4 with a valve, the U-shaped pipe 10 and the main machine 11 were connected to each other. The U-shaped pipe 10 was placed vertically and parallel to the main machine 11. The diameter of the U-shaped pipe 10 was 0.5 cm, and the height of the U-shaped pipe 10 was 14 cm. Three marking lines were designed on the U-shaped pipe 10 on the side close to the main machine 11. From top to bottom, the first marking line 6 was at a height of 12 cm, the second marking line 7 was at a height of 10 cm, and the third marking line 8 was at a height of 8 cm. The U-shaped pipe 10 was filled with deionized water to a height of 5 cm. The main machine 11 was connected with a vacuum pump and an electrical control device, where the power of the vacuum pump was 50 W.

The upper opening of the filling container was sealed with a large sealing rubber plug. The vacuum pump of the main machine 11 was turned on. The vacuum pump was turned off when the water level on one side of the U-shaped pipe 10 crossed the first marking line 6. The U-shaped pipe was quickly connected to the upper-sealed filling container using the three-way pipe. There was no change in the liquid level for 110 s, and the airtightness of the device was qualified.

The large sealing rubber plug was removed. 3.3 g of the first layer of $ZrO_2$, SiC, $TiO_2$, redispersible latex particles and mullite particles were filled. The particle packing layer was compacted under a pressure of 15 MPa. A total of 10 layers were filled, which had a thickness of about 5 cm.

The vacuum pump was turned on. When the liquid level crossed the second marking line 7, the vacuum pump was turned off. The U-shaped pipe and the filling container were quickly connected using the three-way pipe. The liquid level continued to rise for a certain distance under the action of inertia and then began to fall. When the liquid level dropped to the second marking line, the stopwatch was started for timing. When the liquid level dropped to the third marking line 8 at 23 s, the timing was stopped. The experiment was repeated 3 times, the timing was stopped at 25 s, 22 s and 24 s respectively. The average value of 24 s was used as the final test result. The thickness of the first layer of filled particles was randomly measured three times using a vernier caliper, which were 0.50, 0.49, and 0.48 cm respectively, and 0.49 cm was taken as the final test result. The second layer of $ZrO_2$, SiC, $TiO_2$, redispersible latex particles and mullite particles were filled and compacted in the same way. The data of the test results are listed in Table 3. Finally, the particles filled in the metal container were cleaned up.

The slopes of the ten line segments passing through (0.49, 24) point and (0.97, 55) point, (0.97, 55) point and (1.49, 85) point, and so on, were calculated point-by-point. The arithmetic mean value of the slopes of the ten line segments was calculated, and the result is also listed in Table 3. An indicator that characterizes the actual particle packing gradation was obtained.

The diameter of the neck of the lower part of the metal container was 0.7 cm. The diameter of the air-permeable holes of the air-permeable thin plate 2 was 0.4 mm. The number of the air-permeable round holes was 60/cm$^2$. The air-permeable thin plate 2 was covered with 1 layer of qualitative filter paper.

The bottom of the filling container 1, the connecting pipe 3, the three-way pipe 4 with a valve, the U-shaped pipe 10 and the main machine 11 were connected to each other. The U-shaped pipe 10 was placed vertically and parallel to the main machine 11. The diameter of the U-shaped pipe 10 was 2 cm, and the height of the U-shaped pipe 10 was 20 cm. Three marking lines were designed on the U-shaped pipe 10 on the side close to the main machine 11. From top to bottom, the first marking line 6 was at a height of 18 cm, the second marking line 7 was at a height of 16 cm, and the third marking line 8 was at a height of 10 cm. The U-shaped pipe 10 was filled with deionized water to a height of 7 cm. The main machine 11 was connected with a vacuum pump and an electrical control device, where the power of the vacuum pump was 80 W.

The upper opening of the steel container of the filling device was sealed with a large sealing rubber plug. The vacuum pump of the main machine 11 was turned on. The vacuum pump was turned off when the water level on one side of the U-shaped pipe 10 crossed the first marking line 6. The U-shaped pipe was quickly connected to the upper-sealed filling container using the three-way pipe. There was no change in the liquid level for 100 s, and the airtightness of the device was qualified.

The large sealing rubber plug was removed. 6.0 g of the first layer of mixed particles of quartz sand, dry refractory clay, bauxite clinker particles, and dried diatomaceous earth was filled. The particle packing layer was compacted under

TABLE 3

| | | | | | Data of test in Example 2 | | | | | |
| --- | --- | --- | --- | --- | --- | --- | --- | --- | --- | --- |
| | One layer | Two layers | Three layers | Four layers | Five layers | Six layers | Seven layers | Eight layers | Nine layers | Ten layers |
| Thickness/cm | 0.49 | 0.97 | 1.49 | 2.00 | 2.48 | 2.97 | 3.49 | 3.99 | 4.50 | 4.99 |
| Air permeability time/s | 24 | 55 | 85 | 114 | 139 | 155 | 168 | 178 | 182 | 185 |
| Slope point by point | — | 65 | 58 | 57 | 52 | 33 | 25 | 20 | 8 | 6 |
| Average slope/indicator of gradation | | | | | | 36 | | | | |

Example 3

Industrial raw materials quartz sand, dry refractory clay, bauxite clinker particles, and dried diatomaceous earth were used. The particle size of the quartz sand was 1-2 mm, the particle size of the refractory clay was 0.01-0.10 mm, the particle size of the bauxite clinker particles was within a range of 0.5-0.1 mm, and the particle size of the diatomaceous earth was within a range of 1-0.5 mm. The above particles were evenly mixed according to the weight ratio of 6:2:1:1. The filling part of the filling device had a diameter of 3 cm and a total height of 7 cm. The distance between the air-permeable thin plate 2 and the neck was 2 cm. The filling container 1 and the air-permeable thin plate 2 had a thickness of 1.0 cm. The size of the platform was 5 mm. A depth scale with a minimum scale of 1 mm was engraved on the inner side of the particle filling part of the metal container.

a pressure of 7 MPa. A total of 10 layers were filled, which had a thickness of about 5.5 cm.

The vacuum pump was turned on. When the liquid level crossed the second marking line 7, the vacuum pump was turned off. The U-shaped pipe and the filling container were quickly connected using the three-way pipe. The liquid level continued to rise for a certain distance under the action of inertia and then began to fall. When the liquid level dropped to the second marking line, the stopwatch was started for timing. When the liquid level dropped to the third marking line 8 at 15 s, the timing was stopped. The experiment was repeated 3 times, the timing was stopped at 16 s, 15 s and 15 s respectively. The average value of 15 s was used as the final test result. The thickness of the first layer of filled particles was randomly measured three times using a vernier caliper, which were 0.54, 0.55, and 0.57 cm respectively, and 0.55 cm was taken as the final test result. The second layer of mixed particles of quartz sand, dry refractory clay, bauxite clinker particles, and dried diatomaceous earth was filled and compacted in the same way. The data of the test results are listed in Table 4. Finally, the particles filled in the metal container was cleaned up.

The slopes of the ten line segments passing through (0.55, 15) point and (1.12, 60) point, (1.12, 60) point and (1.67, 95) point, and so on, were calculated point-by-point. The arithmetic mean value of the slopes of the ten line segments was calculated, and the result is also listed in Table 4. An indicator that characterizes the actual particle packing gradation was obtained.

on the side close to the main machine 11. From top to bottom, the first marking line 6 was at a height of 22 cm, the second marking line 7 was at a height of 20 cm, and the third marking line 8 was at a height of 13 cm. The U-shaped pipe 10 was filled with deionized water to a height of 9 cm. The main machine 11 was connected with a vacuum pump and an electrical control device, where the power of the vacuum pump was 400 W.

The upper opening of the steel container of the filling device was sealed with a large sealing rubber plug. The vacuum pump of the main machine 11 was turned on. The vacuum pump was turned off when the water level on one

TABLE 4

| | | | | Data of test in Example 3 | | | | | | |
|---|---|---|---|---|---|---|---|---|---|---|
| | One layer | Two layers | Three layers | Four layers | Five layers | Six layers | Seven layers | Eight layers | Nine layers | Ten layers |
| Thickness/cm | 0.55 | 1.12 | 1.67 | 2.20 | 2.76 | 3.33 | 3.84 | 4.39 | 4.95 | 5.51 |
| Air permeability time/s | 15 | 60 | 95 | 123 | 150 | 174 | 190 | 201 | 210 | 218 |
| Slope point by point | — | 79 | 64 | 53 | 48 | 42 | 31 | 20 | 16 | 14 |
| Average slope/indicator of gradation | | | | | | 41 | | | | |

Example 4

Industrial raw materials cement, fly ash, river sand and gravel were used. The cement was 525 Portland cement. The fly ash was a third-grade fly ash with a particle size ranging from to 100 The river sand was washed off sludge and then dried, which had a fineness modulus of 2.6. The particle size of the gravels was within the range of 5-10 mm. The above particles were evenly mixed according to the weight ratio of 1:2:3:4. The filling part of the filling device had a diameter of 6 cm and a total height of 50 cm. The distance between the air-permeable thin plate 2 and the neck was 2 cm. The thickness of the wall of the metal cylinder container and the metal air-permeable thin plate 2 was 1.2 cm. The size of the platform was 12 mm. A depth scale with a minimum scale of 1 mm was engraved on the inner side of the particle filling part of the metal container. The diameter of the neck of the lower part of the metal container was 1.0 cm. The diameter of the air-permeable holes of the air-permeable thin plate 2 was 0.5 mm. The number of the air-permeable round holes was 70/cm². The air-permeable thin plate 2 was covered with 2 layers of qualitative filter paper.

The bottom of the filling container 1, the connecting pipe 3, the three-way pipe 4 with a valve, the U-shaped pipe 10 and the main machine 11 were connected to each other. The U-shaped pipe 10 was placed vertically and parallel to the main machine 11. The diameter of the U-shaped pipe 10 was 3 cm, and the height of the U-shaped pipe 10 was 25 cm. Three marking lines were designed on the U-shaped pipe 10 side of the U-shaped pipe 10 crossed the first marking line 6. The U-shaped pipe was quickly connected to the upper-sealed filling container using the three-way pipe. There was no change in the liquid level for 120 s, and the airtightness of the device was qualified.

The large sealing rubber plug was removed. 79 g of the first layer of mixed particles of cement, fly ash, river sand and gravel was filled. The particle packing layer was compacted under a pressure of 1 MPa. A total of 15 layers were filled, which had a thickness of about 45 cm.

The vacuum pump was turned on. When the liquid level crossed the second marking line 7, the vacuum pump was turned off. The U-shaped pipe and the filling container were quickly connected using the three-way pipe. The liquid level continued to rise for a certain distance under the action of inertia and then began to fall. When the liquid level dropped to the second marking line, the stopwatch was started for timing. When the liquid level dropped to the third marking line 8 at 19 s, the timing was stopped. The experiment was repeated 3 times, the timing was stopped at 18 s, 19 s and 20 s respectively. The average value of 19 s was used as the final test result. The thickness of the first layer of filled particles was randomly measured three times using a vernier caliper, which were 3.01, 2.99, and 3.02 cm respectively, and 3.01 cm was taken as the final test result. The second layer of mixed particles of cement, fly ash, river sand and gravel was filled and compacted in the same way. The data of the test results are listed in Table 5. Finally, the particles filled in the metal container were cleaned up.

TABLE 5

| | | | | Data of test in Example 4 | | | | | |
|---|---|---|---|---|---|---|---|---|---|
| | One layer | Two layers | Three layers | Four layers | Five layers | Six layers | Seven layers | Eight layers | Nine layers |
| Thickness/cm | 3.01 | 6.08 | 9.05 | 12.02 | 15.00 | 18.06 | 21.11 | 24.06 | 27.05 |
| Air | 19 | 63 | 103 | 138 | 170 | 200 | 226 | 250 | 271 |

TABLE 5-continued

| Data of test in Example 4 | | | | | | | | |
|---|---|---|---|---|---|---|---|---|
| permeability time/s | | | | | | | | |
| Slope point by point | — | 14 | 13 | 12 | 11 | 10 | 9 | 8 | 7 |
| Average slope/indicator of gradation | | | | | 8 | | | | |

| | Ten layers | Eleven layers | Twelve layers | Thirteen layers | Fourteen layers | Fifteen layers |
|---|---|---|---|---|---|---|
| Thickness/cm | 30.10 | 33.01 | 36.05 | 39.02 | 42.10 | 45.09 |
| Air permeability time/s | 291 | 309 | 325 | 340 | 350 | 359 |
| Slope point by point | 7 | 6 | 5 | 5 | 3 | 3 |
| Average slope/indicator of gradation | | | 8 | | | |

The slopes of the fifteen line segments passing through (3.01, 19) point and (6.08, 63) point, (6.08, 63) point and (9.05, 103) point, and so on, were calculated point-by-point. The arithmetic mean value of the slopes of the fifteen line segments was calculated, and the result is also listed in Table 5. An indicator that characterizes the actual particle packing gradation was obtained.

The present invention has been exemplarily described above in conjunction with the drawings. Apparently, the specific implementation of the present invention is not limited by the above embodiments. Various insubstantial improvements made using the method, concept and technical solution of the present invention, or direct application of the concept and technical solution of the present invention in other occasions without improvement all fall within the protection scope of the present invention.

The invention claimed is:

1. An experimental method for characterizing particle packing gradation using an experimental device for characterization of particle packing gradation, comprising the following steps:

Step 1. filling a first layer of fillers in a filling container;

Step 2. controlling a three-way pipe with a valve to connect a vacuum pump to a U-shaped pipe, the U-shaped pipe having a first marking line, a second marking line, and a third marking line, and turning on the vacuum pump until a liquid level crosses the second marking line;

Step 3. controlling the three-way pipe with the valve to connect the filling container to the U-shaped pipe, and starting timing when the liquid level drops to the second marking line;

Step 4. stopping timing when the liquid level drops to the third marking line;

Step 5. repeating steps 2-4 until reaching a preset number of repeated measurements, and taking an arithmetic mean as the final test result; and Step 6. repeating steps 1-5 for a second layer of the fillers with a different thickness until the number of filler layers reaches a designed number of layers of differing thicknesses;

wherein: the device is provided with the filling container having an upper opening, an air-permeable thin plate is arranged in the filling container, the air-permeable thin plate is densely covered with air-permeable round holes, a bottom of the filling container communicates with a top of a connecting pipe, a bottom of the connecting pipe is connected to one end of the U-shaped pipe, the first, second, and third marking lines are provided on a pipe wall of the U-shaped pipe on the side of the connecting pipe, the connecting pipe is provided with the three-way pipe with the valve, and the three-way pipe with the valve is connected to the vacuum pump in a main machine through a bypass.

2. The experimental method for characterizing particle packing gradation according to claim 1, wherein: in the step 1, the thickness of each filler layer is 1.1-2.0 times the maximum particle size of the particles, the minimum thickness is 0.5 cm, each filler layer is compacted under a pressure of 1-20 MPa, and the total thickness of the fillers stacked layer-by-layer is 8-20 times the thickness of a single layer;

in the step 5, the number of repeated measurements is 3-5, and if the error of each repeated measurement is 1-2 s, it is qualified, otherwise it is unqualified.

3. The experimental method for characterizing particle packing gradation according to claim 1, wherein: before the experiment, it is necessary to test the airtightness of the device, during the test, a liquid is injected into the U-shaped pipe, the upper opening of the filling container is sealed with a large rubber plug, the U-shaped pipe is connected to the connecting pipe with a rubber plug, the vacuum pump is connected to the U-shaped pipe by controlling the three-way pipe with a valve, the vacuum pump is turned on, the vacuum pump is turned off when the water level on one side of the U-shaped pipe crosses the first marking line, the U-shaped pipe is quickly connected to the upper-sealed filling container using the three-way pipe, and if there is no change in the liquid level for the set time, the airtightness of the device is qualified, and the characterization experiment of particle packing gradation can be carried out;

the corresponding values of the packing thickness and air permeability time are obtained through the experimental method for characterizing particle packing gradation, so as to obtain the matching relationship between the specific value and the packing gradation index.

4. The experimental method for characterizing particle packing gradation according to claim 1, wherein: the filling container has a cylindrical or cuboid structure, the inner wall of the filling container is provided with a protruding platform for supporting an air-permeable thin plate, the air-permeable thin plate is placed on the platform, the distance between the air-permeable thin plate and the top of the connecting pipe is 1-2 cm, the thickness of the filling container wall and the thickness of the air-permeable thin plate are 0.5-1.5 cm, the thickness of the platform is 0.1-1.0 times the thickness of the filling container wall, the filling container above the air-permeable thin plate is provided with a depth scale on the inner wall, the minimum scale of the depth scale is 1 mm, the filling container is used for holding particles, the particle size of the particles is within the range of 0.01 μm-2 cm, the inner diameter of the filling container is 2-20 times the maximum particle size of the particles held in the filling container, the minimum inner diameter of the filling container is 2 cm, the height of the filling container above the air-permeable thin plate and the thickness of the filler layer are in a ratio of 1.0-1.5, the filling container and the connecting pipe are integrally cast and formed, and the area between the bottom of the platform of the filling container and the connecting pipe has a bucket-shaped structure with a large top and a small bottom.

5. The experimental method for characterizing particle packing gradation according to claim 4, wherein: the number of the air-permeable round holes on the air-permeable thin plate is 20-70 holes/cm², the diameter of the air-permeable round holes is 0.1-0.5 mm, 1-3 layers of qualitative filter paper are placed on the air-permeable thin plate, and the device is provided with a bracket supporting the filling container.

6. The experimental method for characterizing particle packing gradation according to claim 1, wherein: the connecting part of the connecting pipe and the U-shaped pipe is provided with a rubber plug, the center of the rubber plug is provided with a through hole, the bottom of the connecting pipe is inserted into the through hole, the outer edge of the rubber plug is inserted into the U-shaped pipe, and the rubber plug provides the connecting part of the connecting pipe and the U-shaped pipe with airtightness.

7. The experimental method for characterizing particle packing gradation according to claim 6, wherein: the diameter of the U-shaped pipe is 3-50 times the maximum particle size of the particles, the height of the U-shaped pipe is 20-600 times the maximum particle size of the particles, three marking lines are provided, which are, from top to bottom, the first marking line, the second marking line, and the third marking line, wherein the first marking line is at a position 0.8-0.9 times the total height of the U-shaped pipe, the second marking line is at a position 0.7-0.8 times the total height of the U-shaped pipe, and the third marking line is at a position 0.5-0.7 times the total height of the U-shaped pipe.

8. The experimental method for characterizing particle packing gradation according to claim 7, wherein: the U-shaped pipe is filled with a liquid to a height 0.3-0.5 times the total height of the U-shaped pipe, and the liquid is deionized water or pure water.

9. The experimental method for characterizing particle packing gradation according to claim 1, wherein: a vacuum pump and a power supply are fixed inside the casing of the main machine, a screen for displaying time is provided on the surface of the casing, the power supply supplies power for the vacuum pump and the screen, a button area is provided on the surface of the casing, and buttons for controlling timing and running of the vacuum pump are arranged in the button area.

\* \* \* \* \*